(12) United States Patent
Fitzgerald et al.

(10) Patent No.: US 6,269,813 B1
(45) Date of Patent: Aug. 7, 2001

(54) TRACHEAL GAS INSUFFLATION BYPASS AND PHASIC DELIVERY SYSTEM AND METHOD

(75) Inventors: Peter M. Fitzgerald, Parker; Jeffrey T. Sawyer, Lakewood; Michael V. Weadley, Westminster, all of CO (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/232,277

(22) Filed: Jan. 15, 1999

(51) Int. Cl.[7] .................................................. A61M 16/00
(52) U.S. Cl. ............................. 128/207.16; 128/200.26; 128/207.29; 128/912
(58) Field of Search .................. 128/200.26, 207.14, 128/207.16, 207.29, 205.24, 912

(56) References Cited

U.S. PATENT DOCUMENTS

| | | | | |
|---|---|---|---|---|
| 3,366,109 | * | 1/1968 | McAllister | 128/207.16 |
| 3,682,166 | * | 8/1972 | Jacobs | 128/207.29 |
| 3,794,026 | | 2/1974 | Jacobs | 128/145.8 |
| 4,265,237 | * | 5/1981 | Schwanbom et al. | 128/205.24 |
| 4,417,573 | * | 11/1983 | Devries | 128/205.24 |
| 4,466,433 | * | 8/1984 | Robbins | 128/205.24 |
| 4,646,733 | | 3/1987 | Stroh et al. | 128/207.16 |
| 4,836,199 | * | 6/1989 | Palmer | 128/207.16 |
| 5,040,532 | * | 8/1991 | Alfrey | 128/207.16 |
| 5,101,820 | * | 4/1992 | Christopher | 128/207.14 |
| 5,199,427 | * | 4/1993 | Strickland | 128/207.14 |
| 5,279,549 | * | 1/1994 | Ranford | 128/207.16 |
| 5,303,699 | * | 4/1994 | Bonassa et al. | 128/205.24 |
| 5,596,984 | * | 1/1997 | O'Mahony et al. | 128/205.24 |
| 5,606,968 | * | 3/1997 | Mang | 128/207.14 |
| 5,779,687 | * | 7/1998 | Bell et al. | 128/207.16 |

\* cited by examiner

*Primary Examiner*—Aaron J. Lewis
(74) *Attorney, Agent, or Firm*—Michael W. Haas (57) ABSTRACT

Tracheal gas insufflation (TGI) therapy is performed by a bypass valve and a controller which control a flow of TGI gas to a TGI catheter inserted into an endotracheal tube in the tracheal of a patient. The bypass valve is activated into a pass-through state to admit the TGI gas into the catheter and into a bypass state to divert the TGI gas from the TGI catheter. Potentially dangerous over-pressure may be sensed and the TGI gas flow terminated, but then quickly resumed after the over-pressure condition passes. Selectively applying and diverting the TGI gas allows phasic TGI therapy to be performed using heated and humidified gas and also allows the heat and humidity levels of the TGI gas to be maintained during continuous TGI therapy.

31 Claims, 4 Drawing Sheets

TRACHEAL GAS INSUFFLATION BYPASS AND PHASIC DELIVERY SYSTEM AND METHOD

CROSS-REFERENCE A TO RELATED INVENTION

This invention is related to an invention for "Gas Supplying and Substance Suctioning Relative to a Patient's Trachea," described in an U.S. patent application Ser. No. (08/988605), filed Dec. 10, 1997 by one of the inventors here. The subject matter of this previously filed application is incorporated herein by this reference.

FIELD OF THE INVENTION

The present invention relates to improvements in the field of tracheal gas insufflation (TGI) therapy. More particularly, the present invention relates to selectively terminating and resuming the flow of heated and humidified TGI gas into the lungs of a patient under conditions where desired heat and humidity levels of the TGI gas are maintained. Maintaining the desired heat and humidity levels in the TGI gas is particularly important to patient safety and comfort.

BACKGROUND OF THE INVENTION

Mechanical ventilators are regularly used in the treatment of medical patients who suffer from impaired respiratory function or respiratory failure. Respiratory impairment or failure may result from inadequate ventilatory muscles, chest injury, and lung disease, as well as from a variety of cardiac, neurological, and neuromuscular disorders. In severe cases, a mechanical ventilator is used to completely take over the patient's breathing function by alternately forcing inflation gas into the lungs and thereafter removing exhalation gas from the lungs, thereby regulating the exchange rate of gases in the blood.

Mechanical ventilators typically aspirate at relatively high air volumes and pressures. Recent studies have shown, however, that such use of high air volumes in mechanical ventilators may subject the patient to a number of ventilator-induced lung injuries or volutraumas. In order to lessen the occurrence of these ventilator-induced volutraumas, and for other reasons, a lung protection technique has been utilized which limits the peak alveolar pressure and tidal volume in the lungs, and allows higher concentrations of carbon dioxide in the blood. While this ventilation technique, called permissive hypercapnia, may be tolerated by many patients, it can cause complications in other patients due to acute acidosis, or high acidity in the blood.

One method of decreasing complications due to acute acidosis during permissive hypercapnia involves increasing the removal of carbon dioxide during ventilation by supplying a secondary source of air into the trachea at a higher velocity but lower volume than the mechanical ventilator. This procedure, called tracheal gas insufflation (TGI), creates turbulent airflow in the lungs during exhalation. The turbulence in the lungs increases the amount of carbon dioxide being carried from the lungs with each ventilator induced exhalation, and thereby reduces the acidity in the blood. The turbulence prevents the formation of pockets or dead space volumes of carbon dioxide in the lungs, which might otherwise occur using only the mechanical ventilator for respiration.

TGI is typically accomplished by inserting a gas catheter into the patient's endotracheal tube, and ideally positioning the distal tip of the TGI catheter one to two centimeters from the patient's carina where a branch passage to each lung occurs. This positioning may result in the TGI catheter extending beyond the distal end of the endotracheal tube. An air and oxygen mixture, usually identical to the gas mixture used in the mechanical ventilator, is then introduced into the trachea via the TGI catheter, to cause the turbulence which results in more effective carbon dioxide removal.

One concern associated with both ventilation and TGI is the potential for an occlusion of the endotracheal tube. An occlusion can be particularly dangerous if the endotracheal tube becomes occluded with the tip of TGI catheter positioned beyond the end of the endotracheal tube. When this occurs the gas emitted from the TGI catheter does not have a pathway to escape from the patient's lungs. The continued delivery of TGI gas under such conditions may result in lung tissue damage or a rupture of one or both lungs.

A common cause of occlusions is the accumulation of mucus in the endotracheal tube, although other types of physiological or mechanical occlusions might also occur. To prevent excessive drying of the tissue, damage to the patient's mucus membranes and the accumulation of mucus which might possibly lead to an occlusion, it is desirable to heat and humidify the TGI airoxygen mixture. The heated and humidified gas mixture helps prevent an occlusion from the accumulation of mucus. Mechanical ventilators typically humidify, filter, and warm the inspired gases to avoid or lessen the occurrence of mucus. It is also desirable to heat and humidify the TGI gas mixture, but certain difficulties occur in TGI therapy as a result of heating and humidifying the TGI gas mixture.

Stopping the flow of heated and humidified TGI gas in response to endotracheal tube occlusion or an unexpected pressure increase in the patient's lungs presents a number of problems in TGI therapy. First, a typical TGI heat and humidification device employs a relatively long, electric heating element or wire to heat the humidified gas. The humidified gas passes over the heating element which runs internally along a length of gas hose supplying the TGI catheter. If the gas flow through the hose is stopped, overheating and damage to the hose can occur because the terminated air flow is no longer available to remove residual heat from the heating element. Even a temporary interruption in the gas flow will cause a rise in temperature in the TGI gas, requiring a resumption of the airflow for a relatively lengthy time to reestablish the proper gas temperature operating conditions before the TGI gas can be again delivered to the patient. Second, simply shutting off the heat and humidification device requires the reestablishment of the desired heat and humidity levels before supplying the TGI gas to the patient. Finally, the time required to reestablish the TGI gas flow at the desired conditions after the TGI gas flow is interrupted or after the TGI delivery system is shut off precludes the immediate resumption of TGI therapy, which may induce further trauma in an already-compromised patient.

Another type of TGI therapy is referred to as intermittent or phasic TGI. Phasic TGI therapy involves supplying TGI gas to the TGI catheter and into the trachea only during a portion of the exhalation period of the respiratory cycle created by the mechanical ventilator, but not during the inhalation period of the respiratory cycle. Phasic TGI therapy is considered as offering a potential for therapeutic benefit because the resulting turbulence during exhalation enhances carbon dioxide removal. Phasic TGI also decreases the total gas volume contributed during TGI therapy and allows for simpler operation of the mechanical ventilator.

A significant disadvantage of current phasic TGI therapy is that heated and humidified gas cannot be used due to the problems associated with maintaining the desired heat and humidity levels in the delivered TGI mixture of oxygen and air, as noted above. Consequently, all known phasic delivery TGI therapies use only non-heated and non-humidified air, which may lead to the complications of an increased risk of occlusions from mucus, dried tissue, and damage to the mucus membranes, among other things.

It is with respect to these and other considerations that the present invention has evolved.

SUMMARY OF THE INVENTION

One of the improvements available from the present invention relates to a safety system for selectively and quickly terminating the flow of TGI gas into the patient's lungs in response to an increase in pressure, such as might occur from an unexpected occlusion. Another improvement relates to retaining constant and desired temperature and humidity levels of the TGI gas even after the selective termination of TGI gas flow to the patient's lungs. A further improvement relates to selectively terminating and resuming the flow of the TGI gas mixture to the patient's lungs without disturbing the desired conditions of heat and humidity in the TGI gas. Still another improvement relates to delivering a heated and humidified gas-air mixture during phasic TGI therapy while maintaining constant, desired, steady-state temperature and humidity levels of the TGI gas.

In accordance with these and other improvements, the present invention relates to a tracheal gas insufflation (TGI) therapy delivery apparatus for controlling a flow of TGI gas to a TGI catheter. The TGI therapy delivery apparatus includes a controllable bypass valve connected to the TGI catheter. The bypass valve is operable into a pass-through state to admit the TGI gas into the catheter and operable into a bypass state to divert the TGI gas from the TGI catheter. A controller selectively activates the bypass valve into the pass-through and bypass states. A method aspect of the invention relates to performing tracheal gas insufflation (TGI) therapy on a patient into which a TGI catheter has been inserted. The method comprises the steps of flowing TGI gas into the TGI catheter, and selectively diverting the flow of TGI gas from the catheter and into the ambient atmosphere.

Diverting the flow of TGI gas from the TGI catheter allows an excessive back-pressure condition to be quickly avoided. Furthermore, diverting the flow of TGI gas still maintains a flow condition which will allow the desired levels of heat and humidity in the TGI gas to be sustained, which would not be possible if the flow of gas were terminated. The flow of TGI gas to the TGI catheter may be quickly resumed after diversion, because the heat and humidity levels of the gas are maintained while the gas is diverted. As a result, TGI therapy may be quickly resumed without further compromising the patient. Further still, because of the ability to transition rapidly between the application of TGI gas and the termination of its delivery into the TGI catheter, phasic TGI therapy is conveniently achieved, and the phasic TGI therapy may be practiced with heated and humidified gas.

Other preferred aspects of the invention contribute the following additional improvements. The TGI catheter may be connected via tubing to a pressure transducer located within the controller. A pressure signal from the TGI catheter causes the controller to activate the bypass valve into the bypass state when the pressure signal exceeds a limit value. The control signal may be pneumatic in order to avoid any potential for electrical shock to the patient and to avoid interfering with other electrical equipment connected to the patient. A blender is preferably used to combine air and oxygen as the TGI gas, and the pressurized gas at the blender is a convenient source for pneumatically controlling the bypass valve. The controller preferably calculates a limit value for a safe pressure within the patient's lungs based on the TGI gas flow rate and other factors which may have an influence on the desired pressure level. The bypass valve is preferably of the type which includes a piston member that moves between two positions in response to the pneumatic control signal, thereby establishing the pass-through and bypass states. The by-pass valve is preferably biased to return to the bypass state in the absence of a control signal in order to stop the flow of TGI gas to the patient in the event of an unexpected power or mechanical failure. A heat and humidification device heats and humidifies the TGI gas, and the bypass valve continues the flow of TGI gas without substantial interruption of the heat and humidification levels when activated into the pass-through and bypass states. The controller may further respond to an exhalation phase of a respiratory cycle of the patient and activate the bypass valve into the pass-through state during a predetermined portion of the exhalation phase of the respiratory cycle to accomplish phasic TGI therapy, while activating the bypass valve into the bypass state during the remaining portion of the respiratory cycle. Comparable method steps are also part of the preferred aspects of the invention.

A more complete appreciation of the present invention and its scope can be obtained by reference to the accompanying drawings, which are briefly summarized below, the following detailed description of presently preferred embodiments of the invention, and the appended claims.

DETAILED DESCRIPTION

Figure 1:
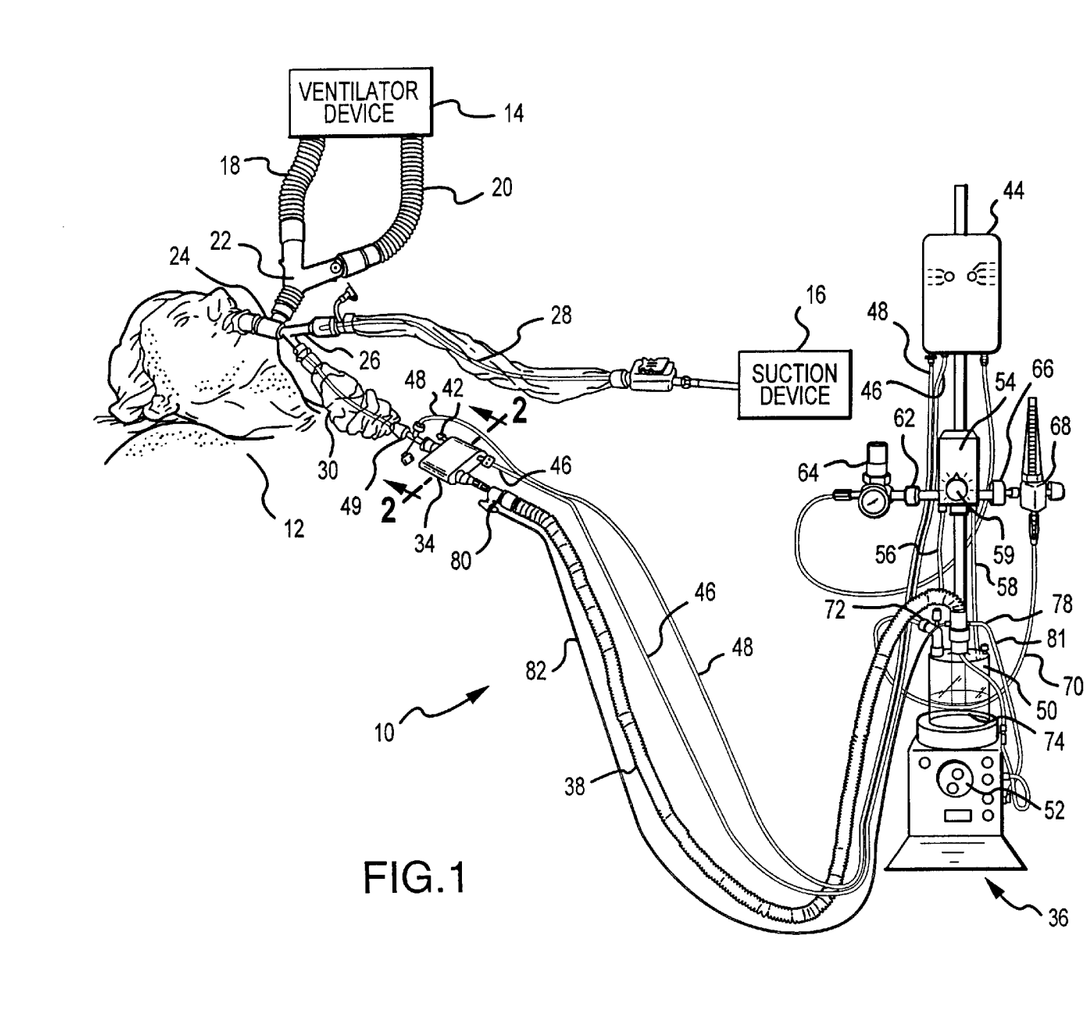
FIG. 1 is an illustration of a TGI therapy delivery system which incorporates the present invention, shown in use with a typical mechanical ventilator device connected to a patient.

A TGI therapy delivery system 10 incorporating the present invention is shown in FIG. 1 connected to a patient 12. The TGI therapy delivery system 10 is used in conjunction with a conventional mechanical ventilator device 14, as well as a conventional suction device 16. The mechanical ventilator device 14 supplies heated, humidified, and oxygenated air through an inhalation hose 18 to the lungs of the patient 12 and extracts carbon dioxide-rich air from the patient's lungs through an exhalation hose 20. The inhalation hose 18 and the exhalation hose 20 are joined at a ventilator Y-piece connector 22. The Y-piece connector 22 is connected to a T-piece connector 24 of the type described in the previously filed U.S. patent application noted above. The T-piece connecter 24 is connected to an endotracheal tube (not shown) which has been medically inserted in the trachea of the patient 12 and to the Y-piece connector 22 to which the ventilator hoses 18 and 20 are connected.

The T-piece connector 24 is also connected to a catheter connection 26, which also has the characteristics described in the previously filed U.S. application noted above. The catheter connection 26 allows access through the T-piece connector 24 to the endotracheal tube for a suction catheter 28 or a tracheal gas insufflation (TGI) catheter 30 to be manually inserted into the trachea of the patient 12 through the T-piece connector 24. The suction catheter 28 is connected to the suction device 16 and when inserted into the endotracheal tube is used to remove mucus or other substances from the lungs of the patient 12. The TGI catheter 30, the suction catheter 28, and the catheter connection 26 are preferably supplied as a single unit, as is described more completely in the previously filed U.S. patent application described above.

The TGI catheter 30 is connected through a TGI bypass valve 34 to a conventional heat and humidification device 36 of the TGI therapy system 10. The heat and humidification device 36 supplies heated and humidified gas to a gas tube 38. The gas tube 38 includes a wire heating element (not specifically shown) which extends along its length to maintain heat in the gas passing through the gas tube 38. The heated and humidified gas is delivered from the gas tube 38 to the TGI bypass valve 34. The TGI bypass valve 34 selectively delivers the heated and humidified TGI gas into the TGI catheter 30 or selectively vents the TGI gas from a vent port 42 into the atmosphere. The flow of heated and humidified gas from the heat and humidification device 36 is thereby maintained in a constant steady-state condition, with the flow continuing either to the TGI catheter 30 or to the atmosphere through the vent port 42.

When the distal tip of the TGI catheter 30 is inserted into the trachea, the heated and humidified TGI gas from the heat and humidification device 36 is passed through the bypass valve 34 into the TGI catheter 30 and into patient's lungs. The TGI gas creates air turbulence and prevents pockets or dead space volumes of carbon dioxide from being formed in the lungs, thereby increasing the removal of carbon dioxide during ventilation.

The TGI bypass valve 34 is preferably controlled by a system controller 44 of the TGI therapy delivery system 10. The system controller 44 delivers a control signal, which is preferably a pneumatic control signal, through a control line 46 which extends between the system controller 44 and the bypass valve 34. A pressure sensing line 48, also preferably a pneumatic line, extends from a connection 49 of the bypass valve 34 and the TGI catheter 30, to the system controller 44. The sensing line 48 senses the pressure in the TGI catheter 30 and delivers a signal (preferably pneumatic) to the system controller 44 in response to the sensed pressure. In a pressure-monitoring safety condition of operation, the system controller 44 recognizes an over-pressure condition, and activates the bypass valve 34 to its bypass state by a control signal sent through the control line 46. In the bypass state, the bypass valve 34 vents the heated and humidified TGI gas to the atmosphere through the vent port 42. In a TGI phasic mode of operation, the system controller 44 may receive additional signals which are used to determine the appropriate time and/or conditions at which to deliver the heated and humidified gas during phasic TGI therapy. The heated and humidified TGI gas is delivered into the TGI catheter 30 and the patient's lungs when the bypass valve 34 is activated into its pass-through state. By selective application of the control signals through the control line 46, the system controller 44 activates the bypass valve 34 into the bypass and pass-through states, to achieve the pressure-monitoring safety and phasic functions described herein, as well as other functions.

The conventional heat and humidification device 36 comprises a humidification chamber 50 and various controls 52 for controlling its operation. The device 36 is connected to a conventional blender 54 which receives air and oxygen from a conventional air source 56 and a conventional oxygen source 58. The blender 54 combines the air and oxygen from the sources 56 and 58 into the TGI gas mixture having the desired proportions of air and oxygen. The air source 56 is preferably a filtered air source within a health care facility, but the air source may also be pressurized ambient air. The oxygen source 58 is from an oxygen bottle or from an internal oxygen source within the health care facility. The proportions of air and oxygen in the final TGI gas mixture are selected by the adjustment of a the blend controller 59 of the blender 54. Typically the air-oxygen mixture from the blender 54 is selected to match the air-oxygen mixture from the mechanical ventilator device 14.

A left (as shown in FIG. 1) output port 62 of the blender 54 is connected to a pressure regulator 64 while a right output port 66 (as shown in FIG. 1) is connected to a flow meter 68. The flow meter 68 controls the flow rate of the air-oxygen mixture supplied by the blender 54 to the humidification chamber 50 of the device 36. The flow meter 68 is connected via a gas line 70 to a pop-off valve inlet 72 of the humidification chamber 50. The air-oxygen mixture from the blender 54 flows through the flow meter 68, the gas line 70 and the pop-off valve inlet 72 and enters the humidification chamber 50, where the gas mixture resides over a pool 74 of sterilized heated water in the chamber 50. The device 36 heats the pool 74 of sterilized water to facilitate the uptake of water into the gas mixture. The gas flow rate from the blender 54 is coordinated with the amount of heat by adjusting the controls 52 of the device 36 to obtain a predetermined level of humidity in the TGI gas mixture as it passes through the humidification chamber 50.

The humidified gas mixture leaves the humidification chamber 50 and passes through the gas tube 38. The gas tube 38 contains the wire heating element (not shown) which runs the length of the tube 38. As the gas mixture passes through the gas tube 38 and around the heating element, its heat is maintained at a preselected temperature in order to avoid vapor condensation in the gas tube 38. The controls 52 of the heat and humidification device 36 control the temperature of the wire heating element within the gas tube 38.

The gas tube 38 contains a first temperature probe 78 at its inflow end which senses the temperature of the gas mixture entering the gas tube 38 and a second temperature probe 80 at its outflow end which senses the temperature of the gas mixture as it exits the gas tube 38. Electrical conductors 81 and 82 respectively connect the first and second temperature probes 78 and 80 to the heat and humidification device 36. A temperature control circuit (not shown) within the device 36 monitors the temperature signals from the two temperature probes 78 and 80 and adjusts the amount of current supplied to the heating element (not shown) in the gas tube 38, thereby adjusting the temperature of the heating element and consequently, the temperature of the TGI gas mixture flowing through the gas tube 38. The control devices 52 of the heat and humidification device 36 control the operation of the device 36 and allow the humidity and temperature levels of the gas mixture to be adjusted in the conventional manner.

Figure 2:
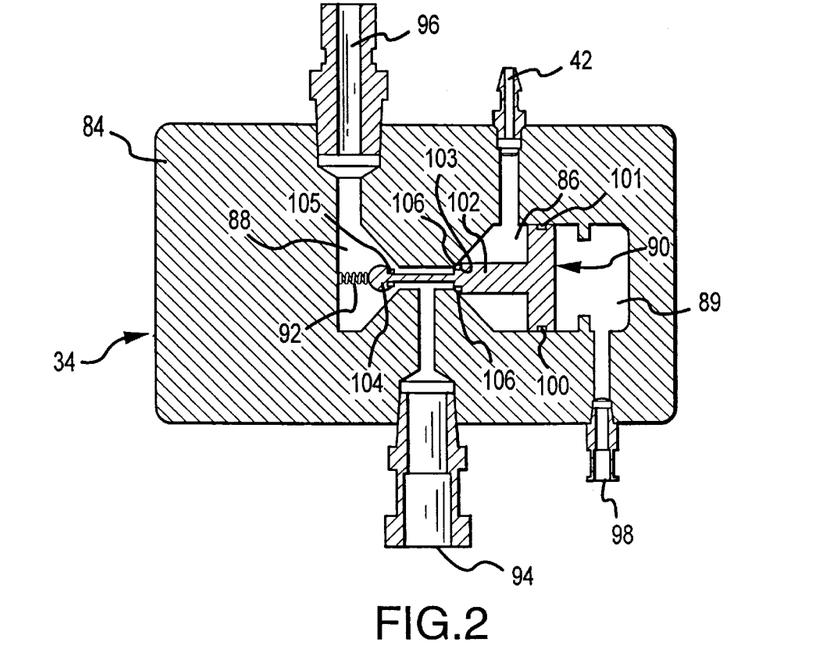
FIG. 2 is a cross-sectional view of a TGI bypass valve assembly of the TGI therapy delivery system shown in FIG. 1, taken generally in the plane of line 2—2 of FIG. 1, and illustrated in a pass-through state.

The heated and humidified air-oxygen gas mixture exiting the gas tube 38 flows into the TGI bypass valve 34. When the bypass valve 34 is in its pass-through state, as shown in FIG. 2, the TGI gas flows into the TGI catheter 30 and into the lungs of the patient 12. To selectively terminate the flow of TGI gas without adversely affecting the desired temperature and humidity levels of the TGI gas, the TGI bypass valve 34 is activated to divert the flow of heated and humidified TGI gas away from the TGI catheter 30 and vent the gas into the atmosphere without changing its flow, temperature, or humidity characteristics. The diversion may be in response to an undesirable buildup of back-pressure in the TGI catheter as sensed through the sensing line 48 or the diversion may be controlled by the system controller 44 during phasic TGI therapy. The diversion may also be controlled manually by the TGI system operator by operating a manual flow bypass control switch 122 (FIG. 4) of the controller 44.

Figure 3:
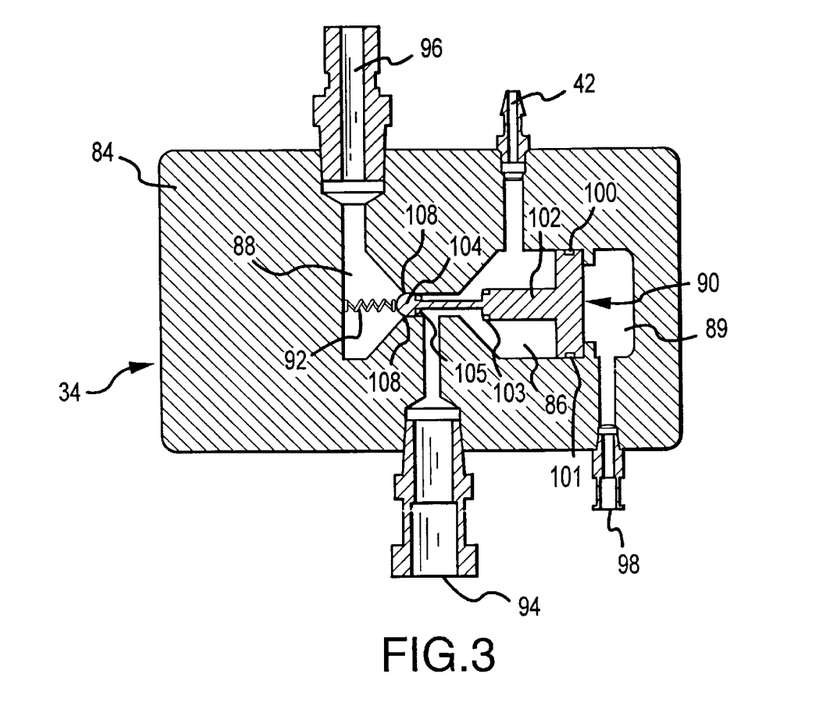
FIG. 3 is a cross-sectional view of the TGI bypass valve shown in FIG. 2, illustrated in a bypass state.

The TGI bypass valve 34 is of the conventional nature of a pressure piloted valve, as shown in FIGS. 2 and 3, and comprises a valve housing 84, a first inner chamber 86, a second inner chamber 88, a third inner chamber 89, a piston member 90, a spring 92, and a number of inlet and outlet ports, including: a TGI gas inlet port 94, a TGI gas outlet port 96, a control port 98, and the TGI vent port 42. The piston member 90 further comprises a piston base portion 100, a piston body portion 102, a piston head portion 104, a base O-ring 101, a body O-ring 103, and a head O-ring 105. The piston member 90 is retained for movement within the chambers 86 and 88, in the right hand and left hand directions, as shown in FIGS. 2 and 3. The spring 92 is positioned between the piston head 104 and the housing 84 in the second chamber 88, and the spring 92 normally biases the piston member 90 to the right hand position (as shown in FIG. 3) which establishes the bypass state of the bypass valve 34.

The gas TGI inlet port 94 is connected to the gas tube 38 (FIG. 1) from which the gas inlet port 94 is supplied with a continuous flow of the heated and humidified TGI gas from the heat and humidification device 36 (FIG. 1). The control port 98 is connected to the control line 46 (FIG. 1) which is connected to the system controller 44 (FIG. 1). The TGI gas outlet port 96 is connected to the TGI catheter 30 (FIG. 1).

The TGI bypass valve 34 is activated into its pass-through state as shown in FIG. 2 by applying pressurized gas into the control port 98. The pressurized gas supplied at the control port 98 originates from the system controller 44 and travels through the control line 46 (FIG. 1) into the third inner chamber 89. The pressurized gas enters the third chamber 89 and applies pressure on the piston base portion 100, causing the piston member 90 to move to the left (as shown in FIG. 2) and overcome the bias force from the spring 92. The piston body portion 102 and the body O-ring 103 are forced against the valve housing 84 at a valve seat 106, thereby sealing the TGI inlet port 94 from fluid communication with the first chamber 86 and the vent port 42. A closed flow path is thereby established through the second inner chamber 88 between the TGI gas inlet port 94 and the TGI gas outlet port 96 which allows the heated and humidified TGI gas to flow from the gas inlet port 94, through the second inner chamber 88, and out the gas outlet port 96 and into the TGI catheter 30 (FIG. 1).

The TGI bypass valve 34 is activated to its bypass state by the absence of pressure applied at the control port 98. The system controller 44 stops the flow of pressurized gas into the control port 98, allowing the spring 92 to push the piston member 90 to the right as shown in FIG. 3. The bias force from the spring 92 forces the piston head 104 and the head O-ring 105 against the valve housing 84 at a valve seat 108, thereby sealing the TGI gas inlet port from fluid communication with the second chamber 88. The path between the gas inlet port 94 and the gas outlet port 96 is thereby closed and a new path is formed from the gas inlet port 94, through the first inner chamber 86, and out the vent port 42. In this condition, as shown in FIG. 3, the bypass valve 34 is in its bypass state. The flow of heated and humidified TGI gas is thereby continued, but the TGI gas is vented to the atmosphere through the vent port 42 rather than to be diverted into the TGI catheter 30 (FIG. 1).

Figure 4:
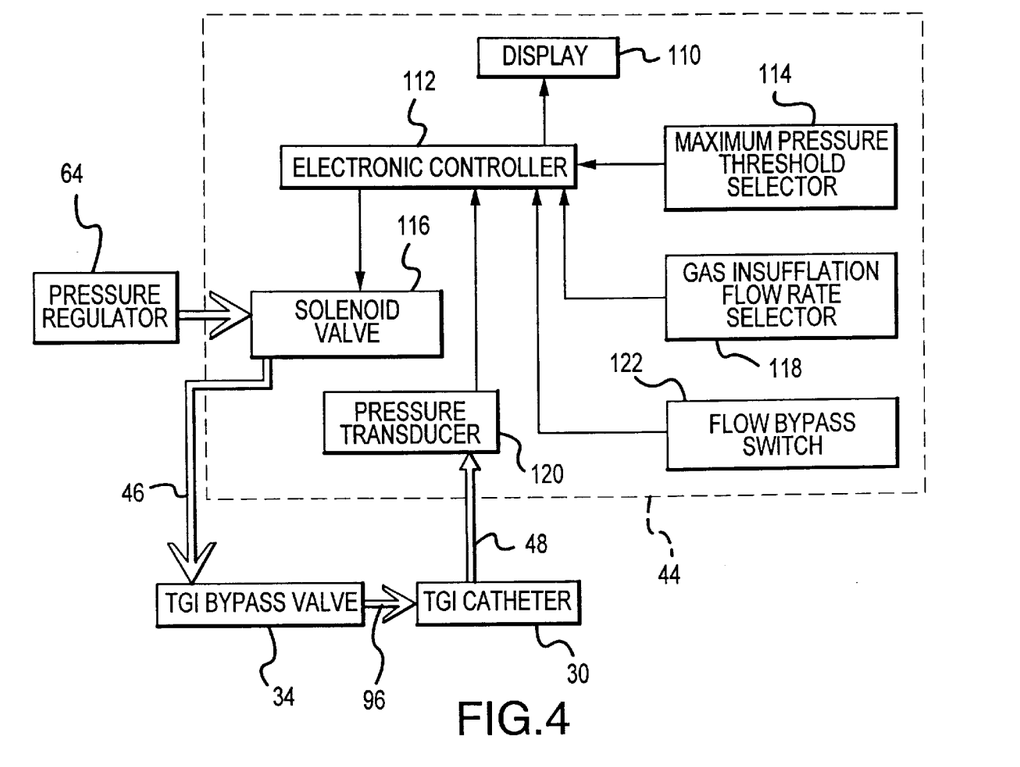
FIG. 4 is a block diagram of a system controller of the TGI therapy delivery system shown in FIG. 1.

The control and operation of the TGI bypass system is performed by the system controller 44, shown in greater detail in FIG. 4. The system controller 44 includes a display 110, an electronic controller 112, a maximum pressure threshold selector 114, a solenoid valve 116, a gas insufflation flow rate selector 118, a pressure transducer 120, and a flow bypass switch 122. The electronic controller 112 may be a conventional microcontroller, microprocessor or an assembly of discrete circuit elements operative to perform the functions described. The system controller 44 controls the opening and closing of the TGI bypass valve 34 in response to pressure levels detected at the TGI catheter 30 in a back pressure safety monitoring mode of operation, and to perform phasic TGI therapy in a phasic mode of operation.

In its back pressure monitoring mode of operation, the electronic controller 112 responds to signals from the gas insufflation flow rate selector 118, responds to signals from the maximum pressure threshold selector 114, and responds to signals from the pressure transducer 120. The flow rate selector 118 is set to a value which coincides with the TGI gas flow rate indicated at the flow meter 68 (FIG. 1). The maximum pressure threshold selector 114 is set to the maximum allowable pressure desired at the TGI catheter 30. The electronic controller 112 processes the signals from the selectors 114 and 118, together with values from a look-up table programmed into memory (not shown) of the electronic controller, and establishes a limit value to which the signal from the pressure transducer 120 is compared. The values in the look-up table are established from empirical characterization studies based on catheter length, catheter internal diameter, and TGI catheter pressures. Using this information, values in the look-up table can be established to relate to safe pressures in the patient's lungs. The values in the look-up table may be programmed at the time of manufacture of the equipment, or later by the user.

If the limit value established by the electronic controller 112 is exceeded by the pressure in the line 48 sensed by the pressure transducer 120, the solenoid valve 116 is closed thus blocking the flow of gas from the pressure regulator 64 into the control port 98 (FIG. 3) of TGI bypass valve 34. The absence of pressurized gas supplied to the TGI bypass valve 34 activates it into its bypass state, diverting the heated and humidified gas away from the TGI catheter 30 and out the vent port 42 (FIG. 3).

By pneumatically controlling the operation of the bypass valve 34 in the manner described, electrical signals are not present near the patient 12. Although a safe electrical signal activation of the bypass valve 34 can be achieved, eliminating the electrical signals near the patient 12 eliminates the possibility of electrical shock and the potential to influence other electrical equipment connected to the patient 12. Furthermore, the pneumatic activation of the bypass valve 34 is an effective and reliable technique by which to change the state of activation of the bypass valve, thereby quickly controlling and relieving any excess pressure which might unexpectedly build in the lungs. The source of pneumatic pressure for controlling the bypass valve 34 is the source of air and oxygen which is readily available and convenient for use in health care facilities.

Figure 5:
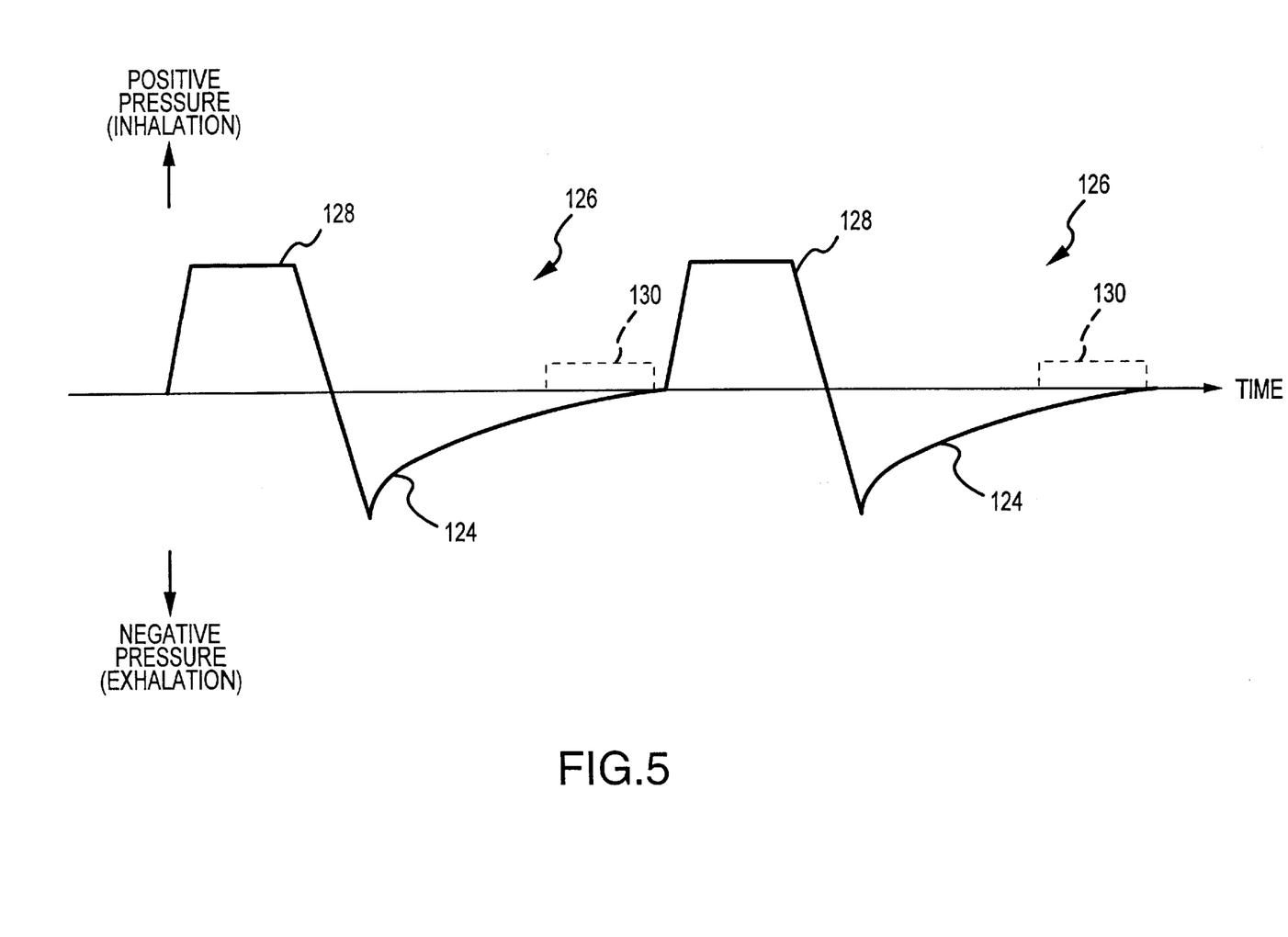
FIG. 5 is a graph of pressure during a series of respiratory cycles created by the mechanical ventilator shown in FIG. 1 and further illustrating the phasic delivery of TGI gas from the TGI therapy delivery system shown in FIG. 1.

The TGI therapy delivery system 10 (FIG. 1) may also be used to deliver intermittent or phasic TGI therapy. Phasic TGI involves delivering TGI gas only during an exhalation phase 124 of a respiratory cycle 126 shown in FIG. 5. The typical respiratory cycle 126 includes an inhalation phase 128 followed by the exhalation phase 124. The mechanical ventilator device 14 exerts positive and negative pressures on the lungs of the patient 12 during the inhalation and exhalation phases 128 and 124, respectively. Phasic TGI therapy involves supplying the TGI gas during a time duration 130 which occurs during the exhalation phase 124 of each respiratory cycle 126. As is known, it is desirable to delay the application of the TGI gas until after the exhalation phase 124 has commenced, and for this reason the time duration 130 begins after the commencement of the exhalation phase 124, as shown in FIG. 5. The system controller 44 (FIG. 1) controls the delivery of the TGI gas for phasic TGI therapy, by activating the bypass valve 34 (FIG. 1) into its pass-through state at the beginning of the time duration 130, and by activating the bypass valve into its bypass state at the ending of the time duration 130.

In order to effectively implement phasic TGI it is necessary to determine when the exhalation phase 124 of the respiratory cycle 126 is taking place. There are a number of methods by which this determination can be made, and by which this information can be communicated to the system controller 44. One method of determining when an exhalation phase 124 is taking place is to place a conventional pneumotach sensor (not shown) in the ventilator exhalation hose 20 (FIG. 1). The sensor sends a signal to the electronic controller 112 in the system controller 44 (FIG. 4) indicating that the exhalation phase 124 of the respiratory cycle 126 is taking place. Another method of determining when an exhalation phase 124 is taking place is for the electronic controller 112 (FIG. 4) to receive a signal from the mechanical ventilator 14 (FIG. 1) when the mechanical ventilator 14 is in the exhalation phase 124.

Once the electronic controller 112 has received a signal indicating that the exhalation phase 124 of the respiratory cycle 126 is taking place, the electronic controller 112 (FIG. 4) then goes through the procedure, as described above, of determining if the pressure in the TGI catheter 30 is less than the limit pressure. If the pressure in the TGI catheter 30 is within acceptable limits, the electronic controller 112 counts time from the commencement of the exhalation phase 124 and then opens the solenoid valve 116 at the commencement of the time period 130, allowing gas from the pressure regulator 64 to flow into the control port 98 of the TGI bypass valve 34. The TGI bypass valve 20 is activated to its pass-through state (FIG. 2), allowing heated and humidified gas to flow from the gas tube 38 and into the TGI catheter 30. Slightly before the end of the exhalation phase 124, as the electronic controller 112 establishes by counting time, the TGI bypass valve is activated to its bypass state, thus terminating the application of the TGI gas at the end of the time period 130. By repeating this process every time a signal indicating that the exhalation phase 124 of the respiratory cycle 126 is taking place, phasic TGI therapy is performed effectively by the TGI therapy delivery system of the present invention.

Thus, the TGI therapy delivery system 10 of the present invention is effective as a safety system for monitoring the pressure in the lungs of a TGI therapy patient, and preventing an unexpected over pressure condition, both in continuous and in phasic TGI therapy. Furthermore, the TGI therapy delivery system maintains a desired level of heat and humidity in the TGI gas, even during the selective termination and resumption of TGI therapy. Because of its ability to maintain that desired heat and humidity levels in the TGI gas, the present invention effectively allows heated and humidified TGI gas to be used in phasic TGI therapy. Many better advantages and improvements will be apparent after fully comprehending the present invention.

Presently preferred embodiments of the invention and its improvements have been described with a degree of particularity.

This description has been made by way of preferred example. It should be understood that the scope of the present invention is defined by the following claims, and should not be unnecessarily limited by the detailed description of the preferred embodiment set forth above.

The invention claimed is:

1. A tracheal gas insufflation (TGI) system, comprising:
    a source of breathing gas;
    a TGI catheter coupled to the source of breathing gas and adapted to deliver a flow of breathing gas to an airway of a patient;
    a controllable bypass valve operatively connected to the TGI catheter and operative in a pass-through state to communicate the flow of breathing gas from the source of breathing gas to an airway of a patient, and operative in a bypass state to divert the flow of breathing gas from the TGI catheter;
    a controller connected to selectively activate the bypass valve into the pass-through state or the bypass state; and
    a pressure sensor operatively connected to the TGI catheter and adapted to supply to the controller a pressure signal related to a pressure in the TGI catheter, and wherein the controller activates the bypass valve into the bypass state in response to the pressure signal exceeding a predetermined value.

2. The TGI system as defined in claim 1, wherein the controller delivers a pneumatic control signal to activate the bypass valve.

3. The TGI system as defined in claim 2, wherein the source of breathing gas includes a blender adapted to combine air and oxygen to produce the flow of breathing gas.

4. The TGI system as defined in claim 1, further comprising a control selector associated with the controller to establish a flow value related to a flow of breathing gas in the TGI catheter and a pressure value related to a maximum pressure level in a patient's lungs during operating of the TGI system, and wherein the controller calculates the predetermined value based on the flow value and the pressure value.

5. The TGI system as defined in claim 2, wherein the bypass valve comprises:
    a housing; and
    a piston member positioned within the housing and moveable between a first position establishing the pass-through state and a second position establishing the bypass state.

6. The TGI system as defined in claim 1, further comprising a humidifier coupled to the TGI catheter to humidify the flow of breathing gas.

7. The TGI system as defined in claim 6 wherein the humidifier includes a humidifying chamber adapted to receive the flow of breathing gas and to contain a pool of water from which humidity is taken up into the flow of breathing gas.

8. The TGI system as defined in claim 1, further comprising a heating element associated with the TGI catheter to heat the flow of breathing gas.

9. The TGI system as defined in claim 8, further comprising a humidifier coupled to the TGI catheter to humidify the flow of breathing gas, and wherein the heating element and humidifier are controlled so as to heat and humidify the flow of breathing gas to predetermined levels.

10. The TGI system as defined in claim 8, wherein the source of breathing gas includes:
    a source of pressurized breathing gas for providing the flow of breathing gas; and
    a tube adapted to deliver the flow of breathing gas from the source of pressurized gas the bypass valve, and wherein the heating element includes a wire extending in the tube to heat the flow of breathing gas passing through the tube.

11. The TGI system as defined in claim 1, wherein, responsive to being in the pass-through state, the controller causes the bypass valve to continuously communicate the flow of breathing gas from the source of breathing gas to an airway of a patient via the TGI catheter regardless of such a patient's respiratory cycle.

12. The TGI system as defined in claim 1, wherein the controller communicates the flow of breathing gas from the source of breathing gas to an airway of a patient via the TGI catheter during at least a portion of an exhalation phase of such a patient's respiratory cycle by placing the bypass valve in the pass-through state and prevents delivery of the flow of breathing gas to an airway of such a patient during a remaining portion of such a patient's respiratory cycle by placing the bypass valve in the bypass state.

13. The TGI system as defined in claim 2, further comprising means for detecting an exhalation phase of a patient's respiratory cycle, and wherein the controller activates the bypass valve in the pass-through state during at least a portion of the exhalation phase and activates the bypass valve in the bypass state during a remaining portion of a respiratory cycle.

14. The TGI system as defined in claim 2, wherein the controller is further operative to respond to an exhalation phase of a plurality of consecutive respiratory cycles of a patient and to activate the bypass valve into the pass-through state during a predetermined portion of each exhalation phase of each respiratory cycle and to activate the bypass valve into the bypass state during a remaining portion of each respiratory cycle.

15. The TGI system as defined in claim 1, further comprising a connector coupled to the TGI catheter to allow for selective alternative insertion of the TGI catheter and a second element into an endotracheal tube inserted in a trachea of a patient.

16. A tracheal gas insufflation (TGI) system, comprising:
    a source of breathing gas;
    a TGI catheter coupled to the source of breathing gas and adapted to deliver a flow of breathing gas to an airway of a patient;
    a controllable bypass valve operatively connected to the TGI catheter and operative in a pass-through state to communicate the flow of breathing gas from the source of breathing gas to an airway of a patient, and operative in a bypass state to divert the flow of breathing gas from the TGI catheter, wherein the bypass valve comprises:
        a housing, and
        a piston member positioned within the housing and moveable between a first position establishing the pass-through state and a second position establishing the bypass state,
        an inlet port adapted to receive the flow of breathing gas from the source of breathing gas,
        an outlet port adapted to supply the flow of breathing gas from the housing to the TGI catheter for delivery to an airway of a patient, and
        a vent port, wherein the inlet port is in fluid communication with the outlet port and is not in fluid communication with the vent port responsive to the piston being in the first position, and wherein the inlet port is in fluid communication with the vent port and is not in fluid communication with the outlet port responsive to the piston being in the second position; and
    a controller connected to selectively activate the bypass valve into the pass-through state or the bypass state.

17. A method of providing a tracheal gas insufflation (TGI) therapy comprising the steps of:
    communicating a flow of breathing gas from a source of breathing gas to an airway of a patient via a TGI catheter;
    providing a controllable bypass valve operatively connected to the TGI catheter, wherein the bypass valve is selectively operative in a pass-through state to communicate the flow of breathing gas from the source of breathing gas to an airway of a patient and a bypass state to divert the flow of breathing gas from the TGI catheter so that the flow of breathing gas is not delivered to an airway of such a patient; and
    selectively activating the bypass valve into the pass-through state or the bypass state, wherein selectively activating the bypass valve further comprising the steps of:
        monitoring a pressure in the TGI catheter,
        comparing the pressure in the TGI catheter to a threshold pressure, and
        diverting the flow of breathing gas from the catheter via the bypass valve by activating the bypass valve in the bypass state responsive to the pressure in the catheter being greater than the threshold pressure.

18. The method as defined in claim 17, wherein communicating a flow of breathing gas includes continuously delivering the flow of breathing gas from the source of breathing gas to an airway of a patient via the TGI catheter during operation of the TGI system regardless of a phase of such a patient's respiratory cycle.

19. The method as defined in claim 17, further comprising the steps of:
    heating and humidifying the flow of breathing gas before communicating the flow of breathing gas to an airway of a patient.

20. The method as defined in claim 17, wherein communicating a flow of breathing gas includes:
    delivering the flow of breathing gas to an airway of a patient only during a predetermined portion of an exhalation phase; and
    diverting the flow of breathing gas flow from the catheter during the remaining portion of each respiratory cycle.

21. A system for providing a tracheal gas insufflation (TGI) therapy to a patient in conjunction with a primary pressure support system that delivers a primary flow of breathing gas to such a patient comprising:

gas flow generating means for providing a flow of breathing gas in conjunction with a primary pressure support system;

delivering means for communicating the flow of breathing gas from the gas flow generating means to an airway of a patient;

bypassing means for selectively diverting the flow of breathing gas from the delivering means so that the flow of breathing gas is not communicated to an airway of a patient;

controlling means for selectively causing the bypass means to divert the flow of breathing gas from the delivery means means for establishing a threshold pressure for a pressure of the flow of breathing gas in the delivery means; and means for determining a pressure of the flow of gas in the delivery means, wherein the controlling means compares the pressure of the flow of gas in the delivery means with the threshold pressure and causes the bypass means to divert the flow of breathing gas from the delivery means responsive to the pressure of the flow of gas in the delivery means exceeding the threshold pressure.

22. The system according to claim 21, further comprising at least one of:

heating means for heating the flow of breathing gas; and humidifying means for humidifying the flow of breathing gas.

23. A system for providing breathing gas to a patient comprising:
   (a) a primary pressure support system comprising:
      (1) a pressure generator adapted to generate a primary flow of breathing gas, and
      (2) a patient circuit coupled to the pressure generator and adapted to carry the primary flow of breathing gas to an airway of a patient; and
   (b) a tracheal gas insufflation (TGI) system comprising:
      (1) a source of TGI gas;
      (2) a TGI catheter coupled to the source of TGI gas and adapted to deliver a flow of TGI gas to an airway of a patient in conjunction with the primary flow of breathing gas;
      (3) a controllable bypass valve operatively connected to the TGI catheter and operative in a pass-through state to communicate the flow of TGI gas from the source of TGI gas to an airway of a patient, and operative in a bypass state to divert the flow of TGI gas from the TGI catheter, and
      (4) a controller connected to selectively activate the bypass valve into the pass-through state or the bypass state.

24. The system according to claim 23, further comprising a pressure sensor operatively connected to the TGI catheter and adapted to supply to the controller a pressure signal related to a pressure in the TGI catheter, and wherein the controller activates the bypass valve into the bypass state in response to the pressure signal exceeding a predetermined value.

25. The system according to claim 23, further comprising a humidifier coupled to the TGI catheter to humidify the flow of TGI gas.

26. The system according to claim 23, further comprising a heating element associated with the TGI catheter to heat the flow of TGI gas.

27. The system according to claim 26, further comprising a humidifier coupled to the TGI catheter to humidify the flow of TGI gas, and wherein the heating element and humidifier are controlled so as to heat and humidify the flow of TGI gas to predetermined levels.

28. The system according to claim 23, wherein, responsive to being in the pass-through state, the controller causes the bypass valve to continuously communicate the flow of TGI gas from the source of breathing gas to an airway of a patient via the TGI catheter regardless of such a patient's respiratory cycle.

29. The system according to claim 23, wherein the controller communicates the flow of TGI gas from the source of TGI gas to an airway of a patient via the TGI catheter during at least a portion of an exhalation phase of such a patient's respiratory cycle by placing the bypass valve in the pass-through state and prevents delivery of the flow of TGI gas to an airway of such a patient during a remaining portion of such a patient's respiratory cycle by placing the bypass valve in the bypass state.

30. The system according to claim 23, further comprising means for detecting an exhalation phase of a patient's respiratory cycle, and wherein the controller activates the bypass valve in the pass-through state during at least a portion of the exhalation phase and activates the bypass valve in the bypass state during a remaining portion of a respiratory cycle.

31. The system according to claim 23, wherein the controller is further operative to respond to an exhalation phase of a plurality of consecutive respiratory cycles of a patient and to activate the bypass valve into the pass-through state during a predetermined portion of each exhalation phase of each respiratory cycle and to activate the bypass valve into the bypass state during a remaining portion of each respiratory cycle.

* * * * *